US005614683A

United States Patent [19]
Kranbuehl

[11] Patent Number: 5,614,683
[45] Date of Patent: Mar. 25, 1997

[54] METHOD AND APPARATUS FOR MONITORING NYLON 11 MADE FROM POLYAMIDE PLASTIC MADE FROM AMINOUNDECANOIC ACID

[76] Inventor: David E. Kranbuehl, 201 Harrison Ave., Williamsburg, Va. 23185

[21] Appl. No.: 571,610

[22] Filed: Dec. 13, 1995

[51] Int. Cl.$^6$ .................................................. G01N 33/00
[52] U.S. Cl. ........................................... 73/866; 73/866.4
[58] Field of Search .................................. 73/866, 866.4, 73/86, 53.05

[56] References Cited

U.S. PATENT DOCUMENTS

| | | | |
|---|---|---|---|
| 3,944,594 | 3/1976 | Kleiner et al. | 260/473 S |
| 3,970,723 | 7/1976 | Mees et al. | 260/880 R |
| 4,483,948 | 11/1984 | Tamosauskas | 523/205 |
| 4,639,997 | 2/1987 | Brull | 29/407 |
| 4,677,159 | 6/1987 | Lahalih et al. | 524/843 |
| 4,957,012 | 9/1990 | Cuddihy et al. | 73/866 |
| 5,174,160 | 12/1992 | Morita et al. | 73/847 |
| 5,305,645 | 4/1994 | Reifsnider et al. | 73/808 |
| 5,317,252 | 5/1994 | Kranbuehl | 324/71.7 |
| 5,331,579 | 7/1994 | Maguire, Jr. et al. | 364/578 |
| 5,377,531 | 1/1995 | Gomm | 73/53.05 |
| 5,455,777 | 10/1995 | Fujiyama et al. | 364/507 |
| 5,470,939 | 11/1995 | Nakae | 528/201 |
| 5,527,835 | 6/1996 | Shustack | 522/42 |

*Primary Examiner*—Hezron E. Williams
*Assistant Examiner*—Jay L. Politzer
*Attorney, Agent, or Firm*—Whitham, Curtis, Whitham & McGinn

[57] ABSTRACT

The molecular weight of NYLON 11® (a polyamide made from aminoundecanoic acid) has been found to be a reliable indicator of the mechanical properties and remaining useful life of parts made therefrom. By periodically monitoring the molecular weight, and comparing the measured molecular weight to a standard curve or table, the expected useful life remaining, rate of deterioration, time of part replacement, and mechanical properties of a part can be determined. The molecular weight may advantageously be determined using witness coupons placed in close proximity to the part such that they are exposed to the same processing and environmental conditions as the part. These witness coupons can advantageously be retrieved at the required time period using a spooled piece of pipe or the like. Alternatively, the molecular weight may advantageously be determined from core samples taken from the part being monitored, during use in the field, on a periodic basis. In addition, the molecular weight might also be inferred from a sample held in a laboratory which is exposed to substantially the same environmental conditions as the part. The molecular weight measurements can be made using standard techniques and equipment such as a viscometer, gel permeation equipment, or light scattering equipments.

17 Claims, 5 Drawing Sheets

METHOD AND APPARATUS FOR MONITORING NYLON 11 MADE FROM POLYAMIDE PLASTIC MADE FROM AMINOUNDECANOIC ACID

BACKGROUND OF THE INVENTION

1. Field of the Invention

The invention is generally related to a system for evaluating the remaining useful life and performance characteristics of parts made from NYLON 11®, a polyamide plastic made from 11-aminoundecanoic acid (hereinafter variously referred to as polyamide formed from aminoundecanoic acid or NYLON® or RILSAN®). More particularly, the invention uses molecular weight measurements to assess the amount of life used or remaining for the part, the rate at which the useable life is changing, and the date at which the part should be replaced.

2. Description of the Prior Art

Life monitoring of plastic and composite parts has become very important in modern industrial processes. Many mechanical parts, including load bearing parts, are now being made of plastic materials because they are lower weight than metals, they do not corrode like metals, they can be more easily formed into desired shapes, they stand up to extreme temperature conditions better than many metals, and for other reasons. However, plastic and composite parts do breakdown and require periodic replacement. In particular, they can become brittle and have reduced tensile strength with time due to exposure to certain chemicals, pH conditions, temperature, exposure to ultraviolet light, and for other reasons. Unlike metal parts, the deterioration of plastic parts is more difficult to assess. For example, weaknesses in metal materials can be assessed by visually detecting cracks and the like; however, cracking in plastic parts is not often a good indicator of structural integrity.

A normal practice in industry is to periodically replace plastic parts before their useful life expires. This is accomplished by conducting aging studies on representative parts, and then establishing a practice of replacing all parts prior to the expiration of a predicted life time for the part. This practice often results in replacing parts well before they are required, which is an expensive proposition in terms of both the material and the time a machine is shut down to replace the part.

Current mechanical testing practices often call for determinations of the percent of extension of a test sample under certain loads, and the load at break of the test sample. Changes in these parameters are then used to assess the fatigue of a part. For example, increases in the percent of extension can indicate that the tensile strength of a part is deteriorating, and decreases in load at break can indicate embrittlement. The difficulty with using this type of mechanical testing of plastic parts in an industrial operation is that the operator can often only tell when the part is no longer useful when it is too late. That is, a part will often perform well up until the point that it breaks and falls apart.

Recently, a few advances have been made in "life monitoring", which refers to a process of assessing the age and/or remaining useful life of a plastic part.

U.S. Pat. No. 5,305,645 to Reifsnider et al. discloses a process for dynamically measuring material strength and life under cyclic loading. Fatigue damage in a specimen is assessed by monitoring signals produced using a dynamic testing machine that applies cyclical loading to a specimen. By analyzing phase differences between displacement and load signals, as well as identifying a change in amplitude of the displacement, the life remaining and residual strength of a sample can be ascertained. Despite its advantages, the Reifsnider et al. technique suffers from the problem of requiring very expensive machinery, and requires specimens to be removed and tested.

U.S. Pat. No. 5,317,252 to Kranbuehl discloses a technique for life monitoring of a plastic part or chemical fluid by monitoring electrical permittivity parameters of a dosimeter. In Kranbuehl, "dosimeters" are described which are applied to the surface of a polymer part being monitored or are simply positioned adjacent the polymer part as a "coupon-type" sensor. In this way, the dosimeter is subjected to the same environment as the part to be monitored (e.g., corrosive fluid handling, light damage, heat damage, etc.). The dosimeter includes a capacitor which undergoes reproducible changes in one or more components of a complex permittivity measurement, and these changes are correlated to a degree of deterioration of the polymeric material being monitored. The approach described in Kranbuehl provides low cost in-situ measurements to be performed; however, it requires a sensor that is selected to undergo reproducible changes in complex permittivity components and requires correlating the changes with the deterioration of a property of interest. Both of these requirements may be difficult to satisfy in certain situations.

SUMMARY OF THE INVENTION

It is an object of this invention to provide a method and apparatus for assessing the amount of life used or remaining for a NYLON 11®(a polyamide made from aminoundecanoic acid) part, the rate at which the useable life of the part is changing, and the date at which the part should be replaced.

It is another object of this invention to provide and method and apparatus for monitoring and scheduling the timely replacement of polyamide formed from aminoundecanoic acid used in oil and gas drilling and transporting operations such as flexible pipes, umbilicals, hoses, metal lined pipes, and the like.

According to the invention, it has been determined that the underlying aging mechanism for mechanical failure of parts made of polyamide formed from aminoundecanoic acid in oil, gas, water and oil-gas-water environments is a chemical degradation of the backbone structure of the polymer chain. Degradation of the chemical backbone results in decreases in molecular weight of the polymer chains. In operation, changes in the molecular weight of a NYLON 11® (a polyamide made from aminoundecanoic acid) part are used to predict the amount of life used or remaining for a part, the rate at which the useable life of the part is changing, and the date at which the part should be replaced. Molecular weight can be assessed by a variety of well known and standard techniques. For example, weight average molecular weight can be determined by light scattering measurements, number average molecular weight can be determined by gel permeation chromatography experiments, and viscosity averaged molecular weight can be determined using a viscometer. Other molecular weight measurement techniques such as osmotic pressure, nuclear magnetic resonance (NMR) imaging, and group analysis may also be used within the practice of this invention.

Experiments have demonstrated that changes in molecular weight of NYLON 11® (a polyamide made from aminoundecanoic acid) have a more profound effect on the mechanical performance of the parts than other factors such as plasticizer diffusion in, water diffusion out, changes in the degree of crystallinity or crystalline structure, or changes in amorphous morphology.

The NYLON 11® (a polyamide made from aminoundecanoic acid) parts can be "monitored" by a variety of methods. For example, witness coupons can be held in close proximity to the part being monitored such that they are exposed to the same process and environmental conditions as the part. Periodically, one of the coupons would be withdrawn for performing molecular weight measurements. Alternatively, the part may be manufactured with regions from which core samples can be periodically obtained and analyzed for changes in molecular weight. Thus, at the time a molecular weight measurement is to be made, a core sample would be obtained from the part. As another alternative, an environmental chamber can be constructed in a laboratory which duplicates the aging process which the part experiences in the field. A test sample which is positioned in the environmental chamber would be periodically analyzed for changes in molecular weight.

Other techniques for monitoring NYLON 11® (a polyamide made from aminoundecanoic acid) parts could also be used within the practice of this invention. The chief requirement to practice the invention would be to provide a mechanism for periodically determining or inferring the molecular weight of in a part being monitored.

As a specific example in a gas/oil operation, witness coupons in a spool piece of pipe can be periodically removed to determine a change in molecular weight, and assess the implications of the molecular weight change on mechanical performance properties. Upon analysis of the molecular weight measurement, useful life remaining, rate of loss of useful life, and time required prior to replacement of the NYLON 11® (a polyamide made from aminoundecanoic acid) part can be determined.

The invention contemplates both the use of a threshold molecular weight measurement to indicate that a part is in need of replacement, and a model for providing a predicted time period for part replacement and for indicating mechanical properties of the part being monitored. With regard to the threshold measurement technique, it has been found that the mechanical performance of NYLON 11® (a polyamide made from aminoundecanoic acid) parts deteriorates to an unacceptable level below a molecular weight threshold of approximately 15,000–20,000 (e.g., 17,000) viscosity averaged molecular weight. Therefore, nylon 11 parts should be replaced once their molecular weight drops below the 15,000–20,000 viscosity averaged molecular weight threshold or any equivalent thereof including weight averaged molecular weight, etc. With regard to the predictive model technique, accelerated aging studies have been conducted with production grade NYLON 11® (a polyamide made from aminoundecanoic acid). In these studies, viscosity averaged molecular weight was the parameter being monitored, and a viscometer was used for the measurements; however, it should be understood that equivalent molecular weight measurements and measurement devices might also be used within the practice of this invention. Production grade NYLON 11®(a polyamide made from aminoundecanoic acid) has a viscosity averaged molecular weight of 50,000±2,000 MW. The experiments demonstrated that the molecular weight decreases for several oil, water environments ranging from 5% water:95% oil to 95% water:5% oil, all at 105° C. and at pH 4.5 over a sixty day period, and that after sixty days at 105° C. and pH 4.5, the molecular weight is below 17,000 and the mechanical properties of NYLON 11® (a polyamide made from aminoundecanoic acid) are unsuitable for most applications (particularly gas and oil drilling applications). By comparing a measured molecular weight for a test sample (e.g., witness coupon, core sample, etc.) with the degradation curve from the accelerated aging studies, the remaining useful life, rate of deterioration, and mechanical properties for the part can be determined. It is envisioned that a family of calibration curves for different pH, temperature and oil compositions would be constructed like the data reported here. Using these calibration curves, an aging molecular weight versus time curve which best describes the aging conditions would be used.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

A series of accelerated aging tests have been carried out on commercially available, production grade NYLON 11®(a polyamide made from aminoundecanoic acid). In the accelerated aging tests, sample coupons were placed in a liquid bath at elevated temperature under pressure. One liquid bath included 95% water by volume and 5% ASTM grade 3 oil by volume saturated with carbon dioxide. The other liquid bath include 95% ASTM grade 3 oil by volume and 5% water by volume saturated with carbon dioxide. Both liquid baths, which each contained oil, water, and carbon dioxide, were kept at a temperature of approximately 105° C. in a closed container at an equilibrium pressure of about 1.2 bar. The elevated temperature was used to create aging over a reasonably short period of time.

The samples used in the aging tests were RILSAN® (a commercial NYLON 11®(polyamide made from aminoundecanoic acid)) BESNO (an oil field in the British Sector of the North Sea owned by SUN OIL®) P40, available from Atochem, and they had a volume averaged molecular weight of approximately 50,000 as determined by viscometer measurements with a Ubbelode viscometer. The samples were cut from a pipe, and were thermo-flattened in a jig. Some "dog bone" style samples were prepared for the mechanical tests. The samples were approximately 6 mm thick and 40 mm square. In the aging baths, the samples were stacked in a small rack to give full exposure on each side.

At pre-determined intervals after the tests were initiated, the aging baths were opened to carry out molecular weight measurements and retrieve triplicate samples for mechanical testing. The mechanical testing was carried out according to ASTM D638. Standard and average values are set forth below. The tests were completed after 150 days of aging.

Figure 1:
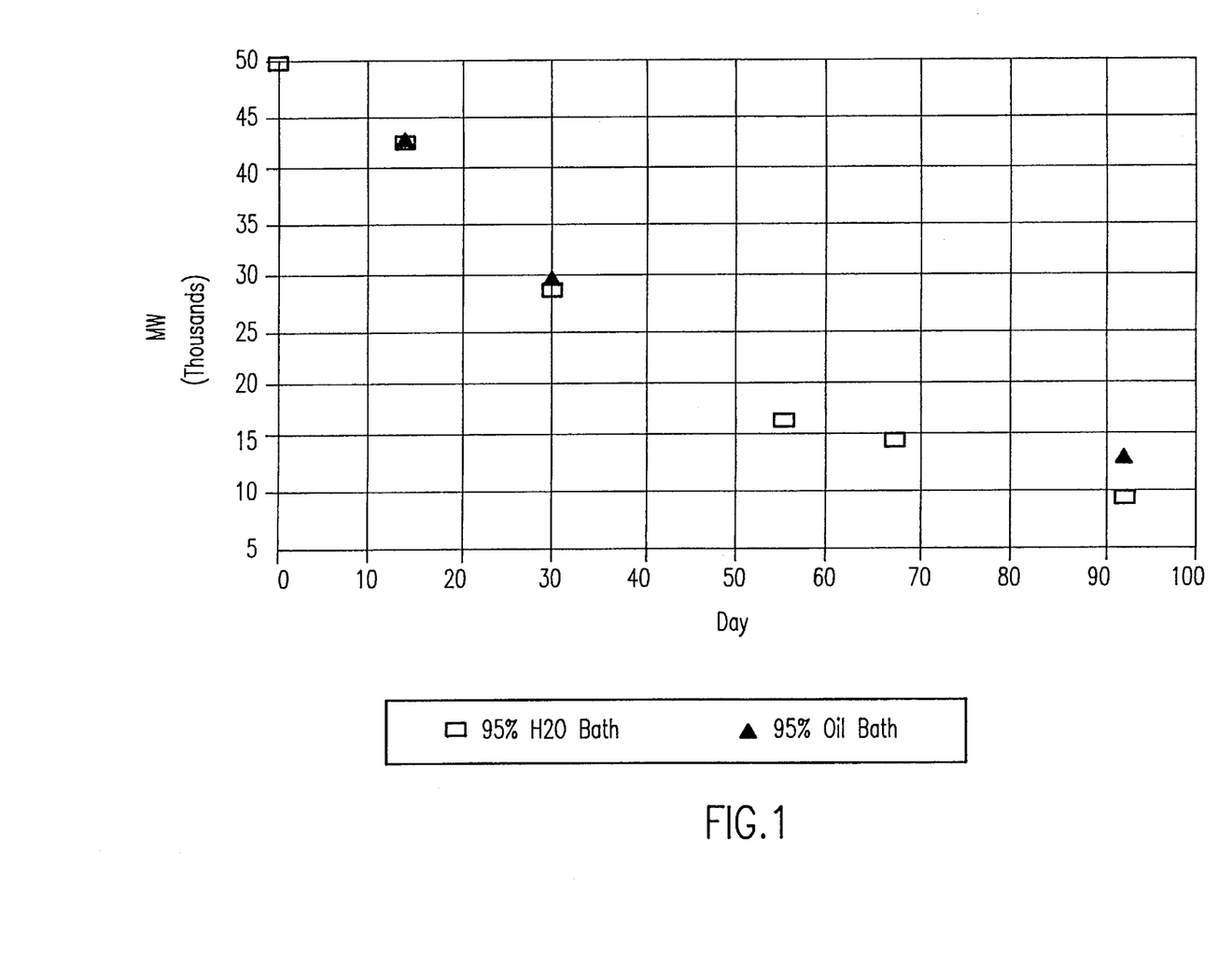
FIG. 1 is a graph showing the relationship of the molecular weight of a NYLON 11® (a polyamide made from aminoundecanoic acid) sample exposed to accelerated aging versus days of the sample in both a 95% water bath and a 95% oil bath, both at pH 4.5 and 105° C.

FIG. 1 shows that the molecular weight of the samples steadily declines from 50,000 to a level below 20,000–15,000 between days 55–70. From Day 60 to Day 150 (not shown), the change in molecular weight is only slight. The decline in molecular weight experienced in the first 60 days of the accelerated aging study is not dependent upon the medium since, as shown in FIG. 1, a curve through test points from Day 1 to Day 60 is approximately the same for both the water bath and the oil bath. Hence, it can be concluded that the aging rate in liquid environments, and particularly in both oil and water environments, is the same.

Figure 2A:
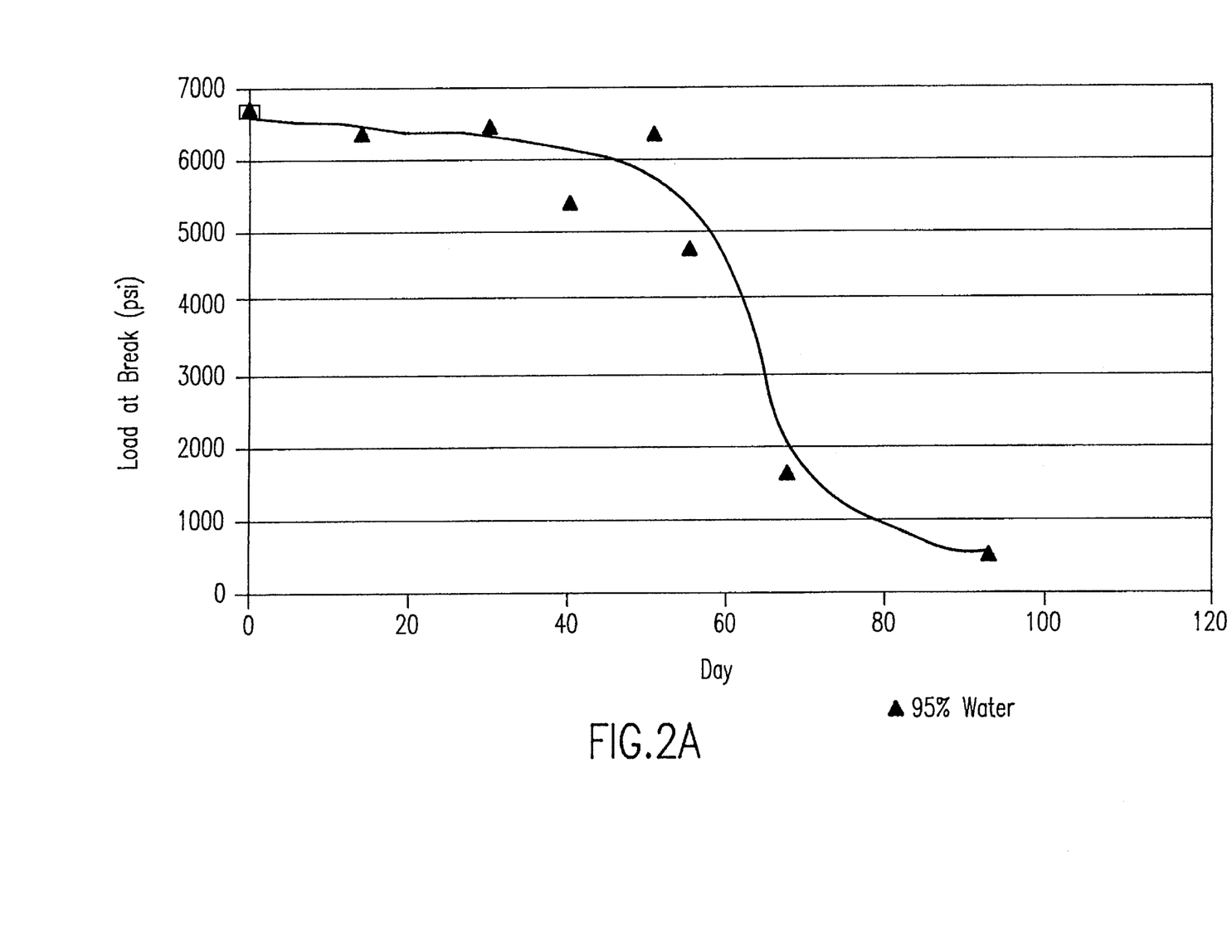
FIGS. 2a and 2b are graphs showing the mechanical properties of aged samples at different days in the accelerated aging study, and particularly show the measured load at break and measure percent extension at break, respectively, for the samples.
Figure 2B:
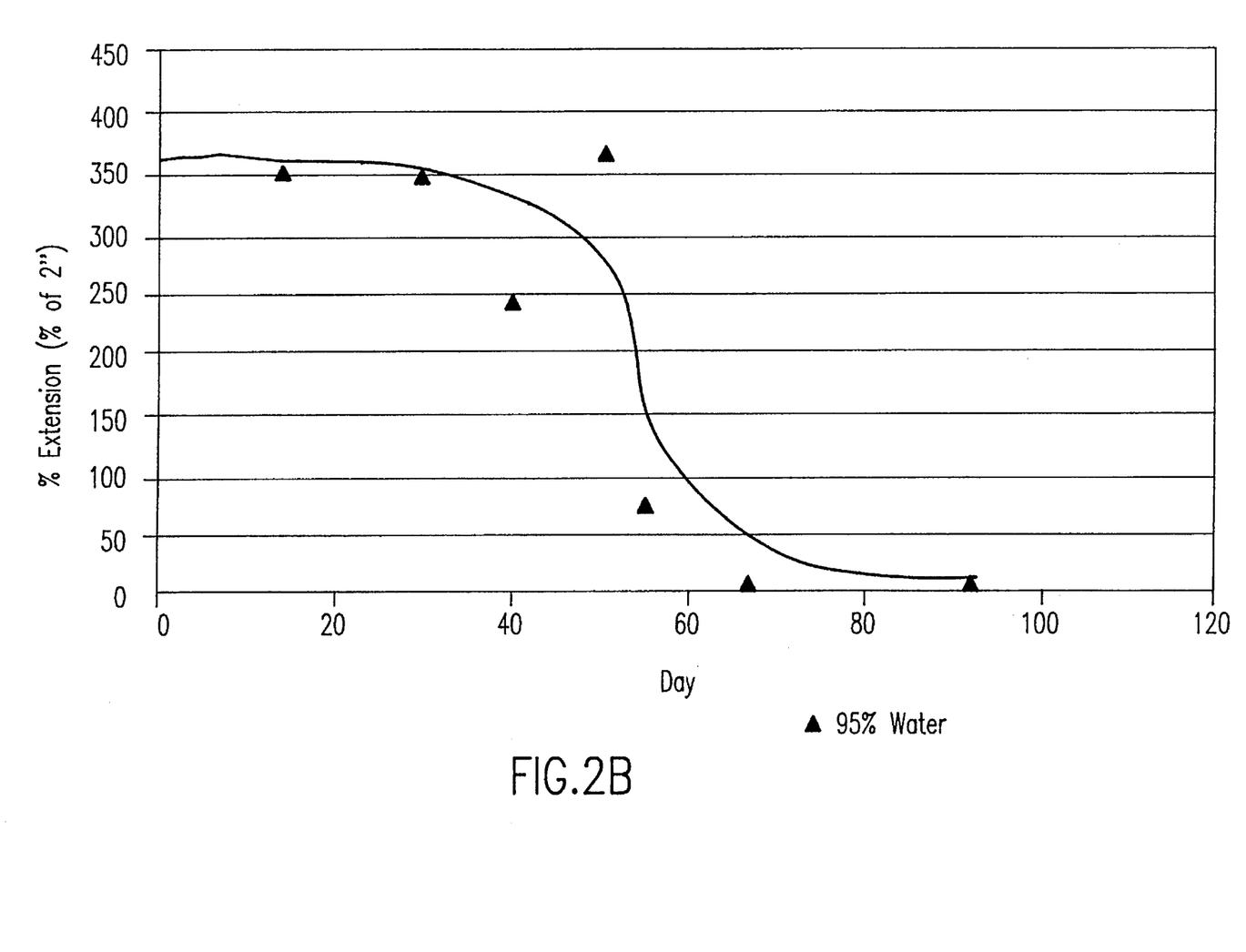

FIGS. 2a and 2b each present the mechanical test results for two combined aging studies wherein FIG. 2a presents load at break data and FIG. 2b presents percent extension at break data determined according to ASTM D638. Each value is the average of three samples. While FIGS. 2a and 2b present test results for water bath experiments, it should be understood that the oil bath experiments presented similar results. The scatter of the mechanical measurements for three nominally identical samples indicated a significant variance demonstrating the uncertainties of these kinds of tests. FIG. 2a shows that the load at break declines dramatically at sixty days. FIG. 2b shows that after sixty days, the elongation at break had dropped to approximately 45% compared to 350% for the virgin material.

FIGS. 2a and 2b show that significant degradation of the NYLON 11 ® (a polyamide made from aminoundecanoic acid) material occurs after sixty days in the accelerated aging study. The mechanical tests demonstrate that the material would no longer, from the point of ductility, be suitable for use in a flexible pipe.

With simultaneous reference to FIGS. 1, 2a, and 2b, it can be seen that the decline in molecular weight corresponds to a decline in mechanical properties. However, of particular importance, it can be seen that the molecular weight measurements are significantly more accurate for assessing the condition of the material than the mechanical measurements. Notably, FIGS. 2a and 2b show that little change in the mechanical properties occur during the initial two thirds of the pipe's useable life. Only when failure is approached do the mechanical measurements provide unambiguous information on age. By contrast, the molecular weight measurements presented in FIG. 1 decline immediately with aging time, and continue to decline until the point of failure (e.g., below 15,000–20,000 (i.e., 17,000) viscosity average molecular weight). Thus, molecular weight measurements provide clear information on aging and rate of aging at all times.

Figure 3A:
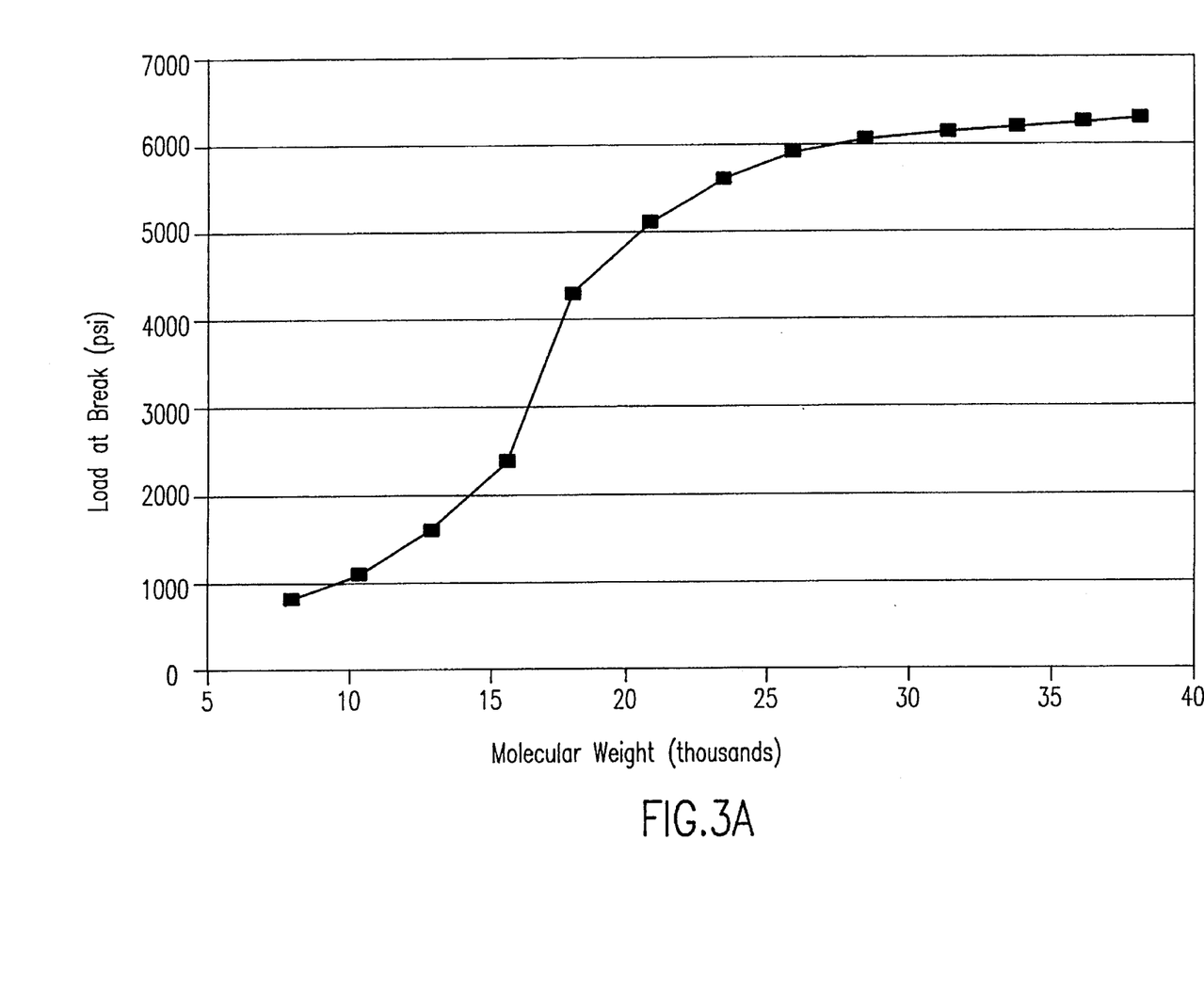
FIGS. 3a and 3b are graphs showing the correlation of molecular weight to the mechanical properties of load at break and percent extension at break, respectively, for the sample materials.
Figure 3B:
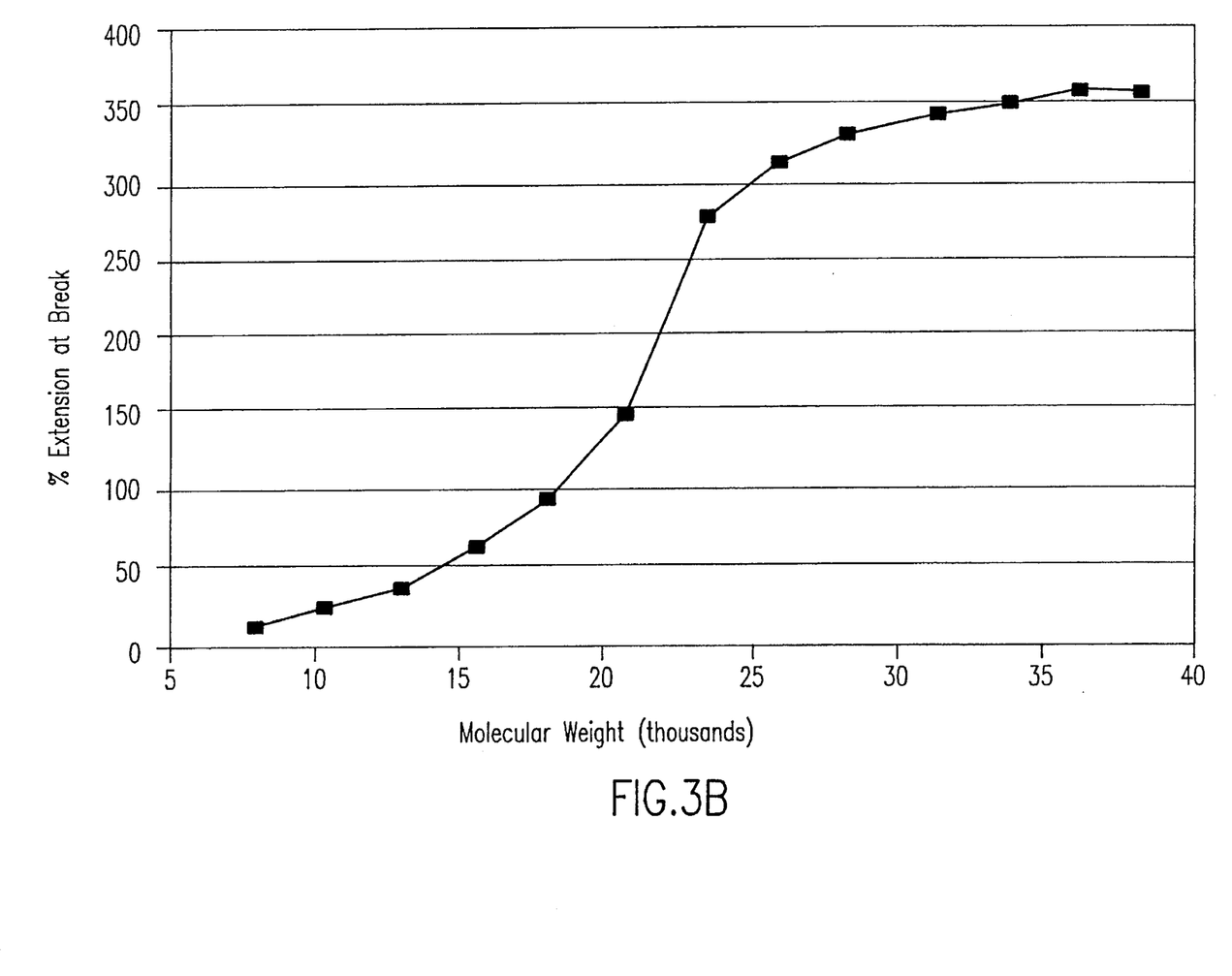

FIGS. 3a and 3b show a correlation of the molecular weight of the samples to the mechanical properties of the load at break and percent extension at break. As discussed above in connection with FIGS. 1, and 2a and 2b, FIGS. 3a and 3b show that molecular weight measurements can be used to assess mechanical attributes of parts made of NYLON 11 ® (a polyamide made from aminoundecanoic acid) material. Based on FIGS. 3a and 3b it is expected that similar correlations can be made between molecular weight and other mechanical properties such as load at yield, percent extension at yield, three point bend results, compression measurements, etc.

In a simple embodiment of the invention, a threshold value for the molecular weight is used to identify a time for part replacement. As can be seen from FIGS. 3a and 3b, the mechanical properties of NYLON 11 ® (a polyamide made from aminoundecanoic acid) having a viscosity averaged molecular weight below approximately 15,000 to 20,000 are deteriorated to a point where they are not suitable for use in many applications (e.g., they are too weak for use in flexible pipes or the like which are used in oil and gas exploration and move in the water currents). However, it should be understood that for pipe which is buried or does not move, this threshold would be lower. Thus, the threshold will vary with the application. While FIGS. 3a and 3b demonstrate a threshold level for viscosity averaged molecular weight, it should be understood by those of skill in the art that equivalent molecular weight measurements such as number average molecular weight, weight averaged molecular weight, etc., can be obtained using other instruments (e.g., gel permeation chromatography in the case of number average molecular weight measurements, and light scattering measurements in the case of weight averaged molecular weight measurements).

In operation, the molecular weight of a part would be periodically determined, and, at such time as the molecular weight drops below a pre-selected threshold level determined by the operator (e.g., 15,000–20,000 viscosity averaged molecular weight), the operator would be directed to replace the part being monitored. The parts can be "monitored" by a variety of methods. For example, witness coupons can be held in close proximity to the part being monitored such that they are exposed to the same process and environmental conditions as the part. Periodically, one of the coupons would be withdrawn for performing molecular weight measurements. Alternatively, the part may be manufactured with regions from which core samples can be periodically obtained and analyzed for changes in molecular weight. Thus, at the time a molecular weight measurement is to be made, a core sample would be obtained from the part. As another alternative, an environmental chamber can be constructed in a laboratory which duplicates the aging process which the part experiences in the field. For example, a test sample would be positioned in the environmental chamber would be periodically analyzed for changes in molecular weight. Other techniques for monitoring NYLON 11 ® (a polyamide made from aminoundecanoic acid) parts could also be used within the practice of this invention. The chief requirement to practice the invention would be to provide a mechanism for periodically determining or inferring the molecular weight of NYLON 11® (a polyamide made from aminoundecanoic acid) in a part being monitored.

In another embodiment of the invention, the percent of life used or remaining for a NYLON 11® (a polyamide made from aminoundecanoic acid) part, and the rate that the useful life of the part is being used are determined from a standard curve such as that which is shown in FIG. 1 for the accelerated aging study (or from a table or other device which relates molecular weight to age). As with the simple embodiment discussed above, molecular weight measurements of parts would be periodically determined. These molecular weight measurements can be made on coupons positioned in close proximity to the part, on core samples taken from the part, or on test samples which are positioned in an environment which replicates the field environment as is described above, or by other means. After the molecular weight measurement is made, the measurement would be compared to a curve or table which correlates molecular weight (e.g., viscosity averaged molecular weight, weight averaged molecular weight, number averaged molecular weight, etc.) with time. By using the molecular weight of the NYLON 11® (a polyamide made from aminoundecanoic acid) at the beginning of its useful life (e.g., the viscosity averaged molecular weight of production grade NYLON 11® (a polyamide made from aminoundecanoic acid) is approximately 50,000±5,000), and using a preselected molecular weight for NYLON 11® (a polyamide made from aminoundecanoic acid) at the end of its useful life (e.g., the viscosity average molecular weight of approximately 15,000–20,000 (i.e., 17,000)), and by determining the time at the beginning of the part's useful life and the time at which the molecular weight measurement is determined, the operator can rapidly and accurately assess the life which has been used up or the life which is remaining, as well as the rate of deterioration of the part.

For example, with reference to FIG. 1, if a part is used in the field 10 years, and the viscosity averaged molecular weight of the part measures approximately 30,000, this corresponds to approximately thirty days on the accelerated aging curve of FIG. 1, and this represents half of the sixty day life span under the accelerated aging study as discussed above. Thus, it can be concluded that half the useful life of the part has been used, that the part has approximately a ten year life span remaining, and that the rate of deterioration is approximately 5% per year. If the part had only been used in the field 5 years, but it still had a viscosity averaged molecular weight of approximately 30,000, it can be concluded that the part has five years of life remaining and that the rate of deterioration is approximately 10% per year.

While FIG. 1 provides data for a viscosity averaged molecular weight measurement, and a sixty day accelerated life span, it will be well understood by those of skill in the art that other forms of molecular weight measurement could be employed (e.g., weight averaged molecular weight, number averaged molecular weight, etc.), and that the standard curve or table developed for accelerated aging that is used for comparison can vary in length (e.g., 1–1000 days, etc.). What will be required to practice the invention will be to have a suitable means to measure the molecular weight, a suitable means to measure the time period from the date of first use, and a suitable standard curve or table which correlates molecular weight to time.

To evaluate the use of molecular weight in assessing the performance of NYLON 11® (a polyamide made from aminoundecanoic acid) parts, field samples of five different aged NYLON 11® (a polyamide made from aminoundecanoic acid) pipes furnished by EXXON® Offshore Oil Division, Houston, Tex., were obtained. The samples were characterized using both mechanical techniques and the molecular weight technique described above.

Table 1 presents a chart of the properties of field aged NYLON 11® (a polyamide made from aminoundecanoic acid) (samples A1, A2, D2, E1, and E2) and compares them to a control (unaged) piece of NYLON 11® (a polyamide made from aminoundecanoic acid) (RILSAN®).

TABLE 1

| PROPERTY | A1 | A2 | D2 | E1 | E2 | C |
| --- | --- | --- | --- | --- | --- | --- |
| Service Duration (yrs) | 8.8 | 8.8 | 5.25 | 0.83 | 5.6 | 0 |
| Max. Temp. (°C.) | 95 | 88.3 | 25 | 91.1 | 79 | n/a |
| ID Hardness | 94.8 | 88.2 | 90.6 | 91.4 | 89.4 | 86 |
| OD Hardness | 92.4 | 84.6 | 85.2 | 83 | 88.2 | 78.6 |

TABLE 1-continued

| PROPERTY | A1 | A2 | D2 | E1 | E2 | C |
| --- | --- | --- | --- | --- | --- | --- |
| Extractable (wt %) | 7.74 | 8.91 | 9.35 | 11.9 | 12.5 | 14.5 |
| Yield Strength (psi) | 4500 | 4645 | 3461 | 3933 | 3744 | 3562 |
| Elong. @ yield (%) | 55 | 59 | 83 | 76 | 81 | 100 |
| Break strength (psi) | 4185 | 4089 | 3753 | 3696 | 4013 | 3975 |
| Elong. @ break | 71 | 97 | 252 | 181 | 257 | 330 |
| Modulus (psi) | 19K | 18K | 11K | 12K | 12K | 11K |

Table 1 required destructive measurements on multiple samples of considerable size. Initial examination of the mechanical properties using traditional methods shows few strong distinctions among the samples. Only the elongation data appears to give meaningful results with large enough differences to allow one to conjecture a ranking of relative strength (e.g., C>E2=D2>E2>A2=A1). While the ranking obtained from Table 1 is plausible due to the aging time and temperature data in the table, the data show a great mix of uncertainty.

Table 2 shows the molecular weight measurements (viscosity averaged molecular weight) of each of the field samples and the control.

TABLE 2

| Sample | MW |
| --- | --- |
| A1 (inside) | 25,400 |
| A1 (outside) | 31,600 |
| A2 (inside-darkest part) | 14,200 |
| A2 (inside) | 13,600 |
| A2 (outside) | 24,900 |
| D2 (inside) | 37,700 |
| D2 (outside) | 43,200 |
| E1 (inside) | 23,500 |
| E1 (outside) | 32,000 |
| E2 (inside) | 21,100 |
| E2 (outside) | 35,100 |
| Control | 51,300 |

Table 2 reports values of molecular weight from both the inside and outside layer of the pipe, as well as reports data for regions of exceptional variation in color. The data in Table 2 clearly shows the relative age and mechanical property retention of these samples to be C>D2>E2=A1=E1>A2.

From the data in Table 2, it can be seen that certain pipes would be identified for replacement using a pre-selected threshold level of 20,000. For example pipe A2 would be identified for repair, and pipes E1 and E2 would be identified as being near the end of their useful life.

From the data in Table 2 it can also be seen that the amount of usable life which has expired or remains can be determined, as well as the rate of aging and the expected date of replacement for the pipe. For example, specimen D2 has a mean MW of 40,500. Using the curve in FIG. 1 as a standard, the MW of 40,500 is equivalent to 19 accelerated aging days of an expected accelerated life of 60 days. Thus, the D2 pipe is 33% into its life, has 66% of its life remaining, is aging at about 6% per year with an anticipated life or 16.7 years, or 11.r years remaining assuming the aging conditions do not change.

With reference back to FIGS. 3a and 3b, it can also be seen that the data in Table 2 may also be used to determine various mechanical properties of the material using a calibration curve or table.

While the invention has been described in terms of its preferred embodiments, those of ordinary skill in the art will realize that the invention can be practiced with considerable modification within the spirit and scope of the appended claims.

I claim:

1. A method for evaluating percent of life remaining, used up, and rate of aging a part made of a polyamide formed from aminoundecanoic acid comprising the steps of:

determining a start time for use of said part made of said polyamide;

measuring a molecular weight of said polyamide, said measuring step being performed at a measurement time;

identifying a use time for said part made of said polyamide by subtracting said start time from said measurement time;

comparing said molecular weight measured during said measuring step to a standard curve or table which correlates molecular weight to time; and assessing life information for said part made of said polyamide as a function of said use time, said molecular weight, and said standard curve or table, said life information being selected from the group consisting of life remaining for said part, life used up for said part, and rate at which life of said part is being used up.

2. The method of claim 1 wherein said step of measuring is performed with a viscometer, and wherein said molecular weight measured during said step of measuring is a viscosity averaged molecular weight.

3. The method of claim 1 wherein said step of measuring further comprises the step of obtaining a sample from said part made of said polyamide, said measuring step being performed on said sample.

4. The method of claim 1 wherein said step of measuring comprises the step of retrieving a witness coupon made of said polyamide from a position where said witness coupon is exposed to an environment identical to said part made of said polyamide, said measuring step being performed on said witness coupon.

5. The method of claim 1 wherein said step of measuring comprises the step of aging a sample of said polyamide in an environment which duplicates or simulates a field environment for said part made of said polyamide, said measuring step being performed on said sample of said polyamide.

6. The method of claim 1 wherein said comparing step includes the step of using a graph as said standard curve or table.

7. The method of claim 1 wherein said comparing step includes the step of using a table as said standard curve or table.

8. The method of claim 1 wherein said step of assessing life information provides a value for life remaining for said part made of said polyamide.

9. The method of claim 1 wherein said step of assessing life information provides a value for life used up for said part made of said polyamide.

10. The method of claim 1 wherein said step of assessing life information provides a value for a rate at which life of said part made of said polyamide is being used up.

11. The method of claim 1 wherein said measuring step, said identifying step, said comparing step, and said assessing life information step are each performed repeatedly at prescribed intervals.

12. The method of identifying a time to replace parts made of a polyamide formed from aminoundecanoic acid in a service environment, comprising the steps of:

measuring a molecular weight of said polyamide for said part made of said polyamide;

determining if said molecular weight from said measuring step is greater than a threshold value; and indicating said part made of said polyamide is in need of replacement if said molecular weight is below said threshold value.

13. The method of claim 12 wherein said step of measuring includes the step of providing a viscosity averaged molecular weight value as said molecular weight, and wherein said determining step includes the step of using 17,000 as said threshold value.

14. The method of claim 12 wherein said step of measuring comprises the step of obtaining a sample from said part made of said polyamide, said measuring step being performed on said sample.

15. The method of claim 12 wherein said step of measuring comprises the step of retrieving a witness coupon made of said polyamide from a position where said witness coupon is exposed to an environment identical to said part made of said polyamide, said measuring step being performed on said witness coupon.

16. The method of claim 12 wherein said step of measuring comprises the step of aging a sample of said polyamide in an environment which simulates a field environment for said part made of said polyamide, said measuring step being performed on said sample of said polyamide.

17. A method of evaluating a part made of a polyamide formed from aminoundecanoic acid, comprising the steps of:

measuring a molecular weight of said polyamide used in said part;

using said molecular weight to assess life information selected from the group consisting of life remaining for said part, life used up for said part, modulus, and elongation and load at yield and break.

* * * * *